US012629008B2

(12) United States Patent
Do et al.

(10) Patent No.: US 12,629,008 B2
(45) Date of Patent: May 19, 2026

(54) ENDOSCOPE COMPRISING A FLEXIBLE INSERTION TUBE AND A BENDING PORTION

(71) Applicant: HOYA CORPORATION, Tokyo (JP)

(72) Inventors: Anh Minh Do, Munich (DE); Wolfgang Mayer, Friedberg (DE)

(73) Assignee: HOYA CORPORATION, Tokyo (JP)

( * ) Notice: Subject to any disclaimer, the term of this patent is extended or adjusted under 35 U.S.C. 154(b) by 309 days.

(21) Appl. No.: 18/030,402

(22) PCT Filed: Aug. 27, 2021

(86) PCT No.: PCT/IB2021/057854
§ 371 (c)(1),
(2) Date: Apr. 5, 2023

(87) PCT Pub. No.: WO2022/074477
PCT Pub. Date: Apr. 14, 2022

(65) Prior Publication Data
US 2023/0363627 A1 Nov. 16, 2023

(30) Foreign Application Priority Data

Oct. 7, 2020 (DE) ..................... 10 2020 126 239.6

(51) Int. Cl.
*A61B 1/005* (2006.01)
*A61B 1/00* (2006.01)

(52) U.S. Cl.
CPC ........ *A61B 1/0056* (2013.01); *A61B 1/00071* (2013.01); *A61B 1/00078* (2013.01); *A61B 1/0057* (2013.01); *A61B 1/0055* (2013.01)

(58) Field of Classification Search
CPC . A61B 1/00071; A61B 1/00078; A61B 1/005; A61B 1/0051; A61B 1/0052;
(Continued)

(56) References Cited

U.S. PATENT DOCUMENTS 4,686,963 A * 8/1987 Cohen .................. A61B 1/0055
138/120
5,018,506 A * 5/1991 Danna .................. A61B 1/0053
92/92
(Continued)

FOREIGN PATENT DOCUMENTS

EP 0422842 A2 4/1991
EP 2979650 A1 2/2016
(Continued)

OTHER PUBLICATIONS

Office Action issued in in European patent application No. 21763417. 9, dated Jul. 17, 2025.
(Continued)

*Primary Examiner* — Ryan N Henderson
(74) *Attorney, Agent, or Firm* — Greenblum & Bernstein, P.L.C.

(57) ABSTRACT

The present invention relates to an endoscope including a flexible insertion tube and a bending portion controllable from a proximal side and being distally connected to the insertion tube, wherein in the bending portion a pull rope runs for a pivoting movement of the bending portion, the pull rope being anchored to the distal end of the bending portion, and wherein a biased elastic element is arranged in the longitudinal direction of the bending portion in parallel to the pull rope.

8 Claims, 8 Drawing Sheets

SECTION III-III

(58) Field of Classification Search
CPC ... A61B 1/0053; A61B 1/0055; A61B 1/0056; A61B 1/0057; A61B 1/0058; A61M 25/0041
See application file for complete search history.

(56) References Cited

U.S. PATENT DOCUMENTS

| | | | |
|---|---|---|---|
| 5,106,381 A * | 4/1992 | Chikama | A61M 25/0138 604/528 |
| 5,140,975 A * | 8/1992 | Krauter | G02B 23/26 600/152 |
| 5,176,126 A * | 1/1993 | Chikama | A61B 1/0055 604/95.04 |
| 5,199,950 A * | 4/1993 | Schmitt | A61M 25/0147 604/95.04 |
| 5,203,319 A * | 4/1993 | Danna | G02B 23/26 600/152 |
| 5,255,668 A * | 10/1993 | Umeda | A61M 25/0147 604/528 |
| 5,336,182 A * | 8/1994 | Lundquist | A61M 25/0147 604/528 |
| 5,345,937 A | 9/1994 | Middleman et al. | |
| 5,855,560 A * | 1/1999 | Idaomi | A61M 25/0136 604/528 |
| 6,585,717 B1 * | 7/2003 | Wittenberger | A61M 25/0144 604/523 |
| 6,585,718 B2 * | 7/2003 | Hayzelden | A61M 25/0141 604/524 |
| 6,605,086 B2 * | 8/2003 | Hayzelden | A61M 25/0147 604/95.04 |
| 7,553,275 B2 * | 6/2009 | Padget | A61B 17/320016 606/1 |
| 7,959,601 B2 * | 6/2011 | McDaniel | A61M 25/0144 604/95.04 |
| 9,101,734 B2 | 8/2015 | Selkee | |
| 9,339,286 B2 * | 5/2016 | Padget | A61B 17/29 |
| 10,383,681 B2 * | 8/2019 | Kleih | A61B 18/1482 |
| 10,702,134 B2 | 7/2020 | Do et al. | |
| 2001/0025134 A1 * | 9/2001 | Bon | A61M 25/0144 600/146 |
| 2002/0026100 A1 | 2/2002 | Ouchi | |
| 2002/0165461 A1 * | 11/2002 | Hayzelden | A61M 25/0141 600/523 |
| 2007/0043261 A1 | 2/2007 | Watanabe et al. | |
| 2007/0135803 A1 | 6/2007 | Belson | |
| 2008/0051802 A1 * | 2/2008 | Schostek | A61B 1/00135 600/101 |
| 2008/0161798 A1 * | 7/2008 | Podmore | A61B 17/00234 606/41 |
| 2009/0171159 A1 * | 7/2009 | Jorgensen | A61B 18/1492 600/139 |
| 2009/0326326 A1 * | 12/2009 | Lin | A61B 1/00071 600/146 |
| 2013/0150673 A1 | 6/2013 | Kakehashi | |
| 2016/0081714 A1 | 3/2016 | Kobayashi et al. | |
| 2017/0086652 A1 | 3/2017 | Nakade et al. | |
| 2021/0059746 A1 * | 3/2021 | Govari | A61B 90/361 |
| 2021/0338045 A1 * | 11/2021 | Crowley | A61B 1/00105 |
| 2022/0022732 A1 | 1/2022 | Do | |
| 2025/0152196 A1 * | 5/2025 | Lädermann | A61B 17/32056 |

FOREIGN PATENT DOCUMENTS

| | | |
|---|---|---|
| JP | S63-252128 A | 10/1988 |
| JP | H04-244131 A | 9/1992 |
| JP | H07-100093 A | 4/1995 |
| JP | H07-163514 A | 6/1995 |
| JP | H07-184836 A | 7/1995 |
| JP | 2002-085332 A | 3/2002 |
| JP | 2004-298446 A | 10/2004 |
| JP | 2010-063887 A | 3/2010 |
| JP | 2017-205436 A | 11/2017 |
| WO | WO 92/14506 A1 | 9/1992 |
| WO | WO 2016/117169 A1 | 7/2016 |

OTHER PUBLICATIONS

First Office Action issued in Chinese Patent Application No. 202180053733.X, dated Apr. 9, 2025, together with an English translation.

Notice of Reasons for Refusal issued in Japanese Patent Application No. 2023-507824, dated Dec. 5, 2023, together with an English translation.

Notice of Reasons for Refusal issued in Japanese Patent Application No. 2024-059190, dated Jan. 7, 2025, together with an English translation.

U.S. Appl. No. 18/030,542 to Anh Minh Do, filed Apr. 6, 2023.

International Search Report issued in International Bureau of WIPO Patent Application No. PCT/IB2021/057854, dated Nov. 8, 2021.

* cited by examiner

SECTION III-III

ENDOSCOPE COMPRISING A FLEXIBLE INSERTION TUBE AND A BENDING PORTION

The present invention relates to an endoscope comprising a flexible insertion tube and a bending portion controllable from a proximal side, the bending portion being distally connected to the insertion tube.

An endoscope of this type can be built with a very small diameter so as to examine also small openings or small spaces, for example.

Usually, the diameter of the bending portion is equal to or slightly different from the diameter of the insertion tube of the endoscope. In the case of endoscopes having a thin insertion tube, the bending portion is correspondingly thin.

However, a thin bending portion frequently has no sufficient interior for the complex constructional designs required for a conventional bending portion. The bending portion of the endoscope can be controlled by the user. For this purpose, the bending portion is controlled, i.e., deflected, by the user from the proximal side of the endoscope.

Accordingly, from prior art various basic designs of the bending portion are known, such as a bending portion of articulated members made from metal or a bending portion made from articulated plastic elements.

In the bending portion of articulated members made from metal, the bending portion consists of a number of complexly shaped metal rings respectively connected by a freely movable connection of annular joints. Said annular joints include hinge pins being offset against their respective adjacent annular joint by 90 or, resp., 180 degrees. The bending portion can pivot upwards and downwards via a number of pivot points. Eyelets are arranged in plural rows at the annular joints on the inside of the deflectable portion. Said eyelets serve as a guideway for pull ropes anchored to the distal end of the deflectable portion. The bending or deflecting movement of the deflectable portion is carried out by the pull ropes being pulled from the proximal side.

Basically, two pull ropes are always required for the movement in one direction (e.g., upwards/downwards), because one pull rope can only accomplish a pulling movement but no thrust movement. Therefore, conventionally two pull ropes are required for the movement in one direction. Correspondingly, four pull ropes are required for the movement in two directions. By the movement in two directions various direction settings (combination of horizontal and vertical bending) can be achieved.

Said complex construction requires an appropriate interior inside the bending portion. If the bending portion is very thin, usually there is not sufficient interior space available.

In the bending portion made of plastic elements which are articulated, i.e., hinged relative to each other, plastic elements produced by injection molding are interconnected and pivotable relative to each other via hinges. Although a bending portion of articulated plastic elements shows a very simple construction, it offers even less interior space than the bending portion of articulated members made from metal. This is due to the fact that the partitions of a plastic member require a particular thickness to ensure sufficient stability and, resp., strength. In addition, also in this case eyelets require much space.

Thus, it is an object of the invention to provide an endoscope comprising a flexible insertion tube and a bending portion in which the bending portion and the insertion tube provide sufficient space in the interior. Furthermore, the bending portion of the endoscope is intended to offer satisfactory functionality.

This object is achieved by an endoscope comprising the features of claim 1. Advantageous developments are the subject matter of the dependent claims.

The invention relates to an endoscope comprising a flexible insertion tube and a bending portion controllable from a proximal side, the bending portion being distally connected to the insertion tube. A pull rope for a pivoting movement of the bending portion runs in the bending portion, the pull rope being anchored to the distal end of the bending portion. In the longitudinal direction of the bending portion, a biased elastic element is arranged in parallel to the pull rope. The biased elastic element also occupies space, but less than the space required by a conventional design with a pull rope and eyelets.

In this endoscope, at least one pull rope can be replaced by a biased elastic element. The desired deflection of the bending portion can be controlled so that only the at least one (remaining) pull rope is actuated (pulled). Since at least one pull rope has been replaced by the biased elastic element, the space of the replaced pull rope can be used for other purposes. Since the space for the replaced pull rope is eliminated, the endoscope may have a thinner design.

The biased elastic element may include a predefined bend toward one side of the bending portion. The predefined bend of the biased elastic element imparts a predefined bend to the bending portion in the non-actuated state. If a pull rope is pulled in the non-actuated state, the bend of the bending portion is changed. If the pull rope is pulled in the non-actuated state, the bending portion can be taken out of the predefined bend.

The predefined bend of the biased elastic element can provide the maximum pivoting of the bending portion toward one side. By pulling the (at least one) pull rope, the bending portion can be returned from the maximum pivoting movement forced toward one side to a smaller pivoting movement. If the pull rope is continued to be pulled, the bending portion can be taken to a straight pivoting movement. If the pull rope is even further continued to be pulled, the bending portion can be taken to a deflection in the direction opposed to the original pivoting direction given in the non-actuated state.

The biased elastic element may be arranged in parallel to the pull rope as a bent rod element having a predefined bend toward one side of the bending portion, and the pull rope may be guided by pull rope guide elements. In this endoscope, at least one pull rope can be replaced by the bent rod element. The bent rod element may be bendable.

The biased elastic element can be arranged in parallel to the pull rope as a spiral spring element or as a combination of a distal guided pull rope and a proximal spiral spring element, the spiral spring element having a predefined bias, and the pull rope can be guided by pull rope guide elements. In this endoscope, at least one pull rope can be replaced by the spiral spring element or the combination of the distal guided pull rope and the proximal spiral spring element.

The bending portion may include a sleeve. The biased elastic element may be a bendable separating element that divides the cross-section of the sleeve into two separate chambers, and in one chamber out of the two chambers separated by the separating element the pull rope can be arranged in the longitudinal direction of the sleeve for a pivoting movement of the bending portion.

In this endoscope, at least one pull rope can be replaced by the bendable separating element. Further, by providing the separating element, a separation of the sleeve into two chambers which serve for guiding the pull rope is realized. The separating element replaces the conventional guiding through eyelets.

The bending portion can be easily divided by the separating element into pull rope ducts extending in the longitudinal direction and being delimited to the radial side. Thus, an endoscope having a bending portion can be provided in a simple and cost-efficient manner. The simple design allows for a particularly small construction size, as the principle of dividing the bending portion by the separating element into separate chambers can be applied to any construction size and in particular to very small endoscope diameters.

In one chamber at least one pull rope is arranged. Already with this minimalist structure, the bending portion can be specifically pivoted by pulling the one pull rope.

The separating element may have a predefined bend toward one side of the bending portion. The predefined bend of the separating element bent in a predefined manner can provide maximum pivoting of the bending portion to one side.

In the chamber out of the two chambers separated by the separating element that is arranged on the outside of the radius of the separating element bent in a predefined manner, the pull rope can be arranged in the longitudinal direction of the sleeve for a pivoting movement of the bending portion.

Thus, by pulling the pull rope the bending portion bent in a predefined manner can be bent toward the side on which the bent bending portion becomes straight. The pull rope can be pulled so far that the bent bending portion aligns to become straight. The pull rope can be pulled even further so that the bent bending portion adopts a bend in the direction opposed to the direction of its initial bend.

The separating element can be anchored, at its proximal side, to the distal end region of the insertion tube. The separating element can be anchored, at its proximal side, to the distal end region of the insertion tube so that its length protruding toward the distal side is predefined. Thus, anchoring can be realized in a safe and reliable way, but also in a simple and low-effort way.

The insertion tube may include an outer cover and, beneath the outer cover, an elastic wire mesh, the proximal side of the separating element being anchored to the distal end region of the wire mesh. The wire mesh incorporated in the insertion tube gives firm support to the proximal side of the separating element.

The proximal side of the separating element may be inserted into or else welded to or glued into the distal end region of the wire mesh.

The sleeve of the bending portion may have an outer diameter of 3 mm or less. In the case of an even smaller design, the sleeve of the bending portion may even have an outer diameter of 1 mm or less. Thus, the endoscope is suitable for particularly small cavities which previously could hardly be examined by a flexible endoscope having a bending portion.

The separating element may be manufactured from spring steel, stainless steel or a flexible plastic material. The material of the separating element imparts bendability to the bending portion. However, the separating element is neither compressible nor expandable. In this way, the length of the bending portion corresponding to the length of the separating element remains the same even if the bending portion is bent.

The sleeve of the bending portion may include a spring element. In this way, both flexibility and the necessary stiffness can be imparted to the sleeve and, thus, to the bending portion. In addition, the bending portion can be configured to be twist-proof (torsion-resistant).

The spring element can be embedded in the sleeve of the bending portion. The material of the sleeve may be plastic or rubber. Thus, the sleeve equipped with the spring element is easy to manufacture. For example, the material of the sleeve may be injection-molded or extruded around the spring element.

The cross-section of the separating element may be configured such that the cross-section of the separating element is wider in a first direction and is narrower in a second direction that is perpendicular to the first direction. The cross-section of the separating element may have a rectangular, oval, elliptic or race-track shape (a so-called stadium shape). The separating element can be bent in the direction of the narrow side of the cross-section. The separating element cannot be bent in the direction of the wider side of the cross-section.

In the chamber arranged on the outside of the bent separating element, one single pull rope may be arranged for a pivoting movement of the bending portion, and in the other chamber arranged on the inside of the bent separating element, no pull rope is arranged. In this design, the diameter can be configured to be even smaller as installation space is required for one single pull rope only.

In the chamber arranged on the outside of the bent separating element, plural pull ropes may be arranged for a pivoting movement of the bending portion. Furthermore, there may be no pull rope arranged in the other chamber disposed on the inside of the bent separating element. In this design, the pivoting movement of the bending portion can be safely carried out.

The endoscope may be a flexible endoscope.

Hence, according to the present invention, bending in one direction (to the front and the rear or to the right and the left) is ensured by only one pull rope and one additional element and the bending unit. In a further development, the present invention offers bending in all directions (to the front and the rear and to the right and the left, and, correspondingly, all intermediate stages due to combined pulling) by two pull ropes and two additional elements. An additional element in this case is understood to be, e.g., a spring element or a spring rod.

The afore-explained aspects of the present invention can be combined as appropriate.

Figure 1:
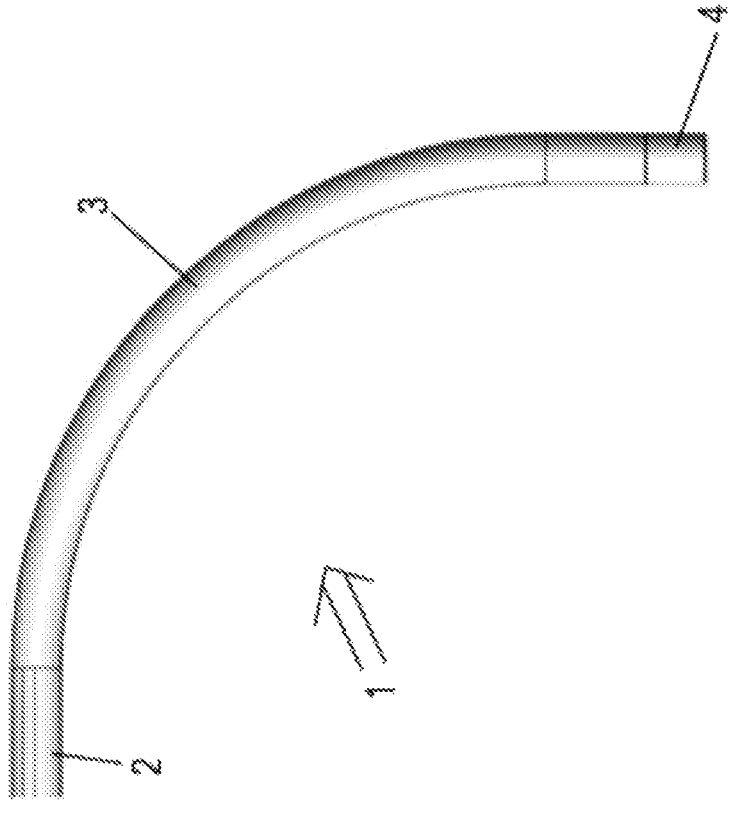
FIG. 1 shows a schematic side view of a distal region of an endoscope according to the invention.
Figure 2:
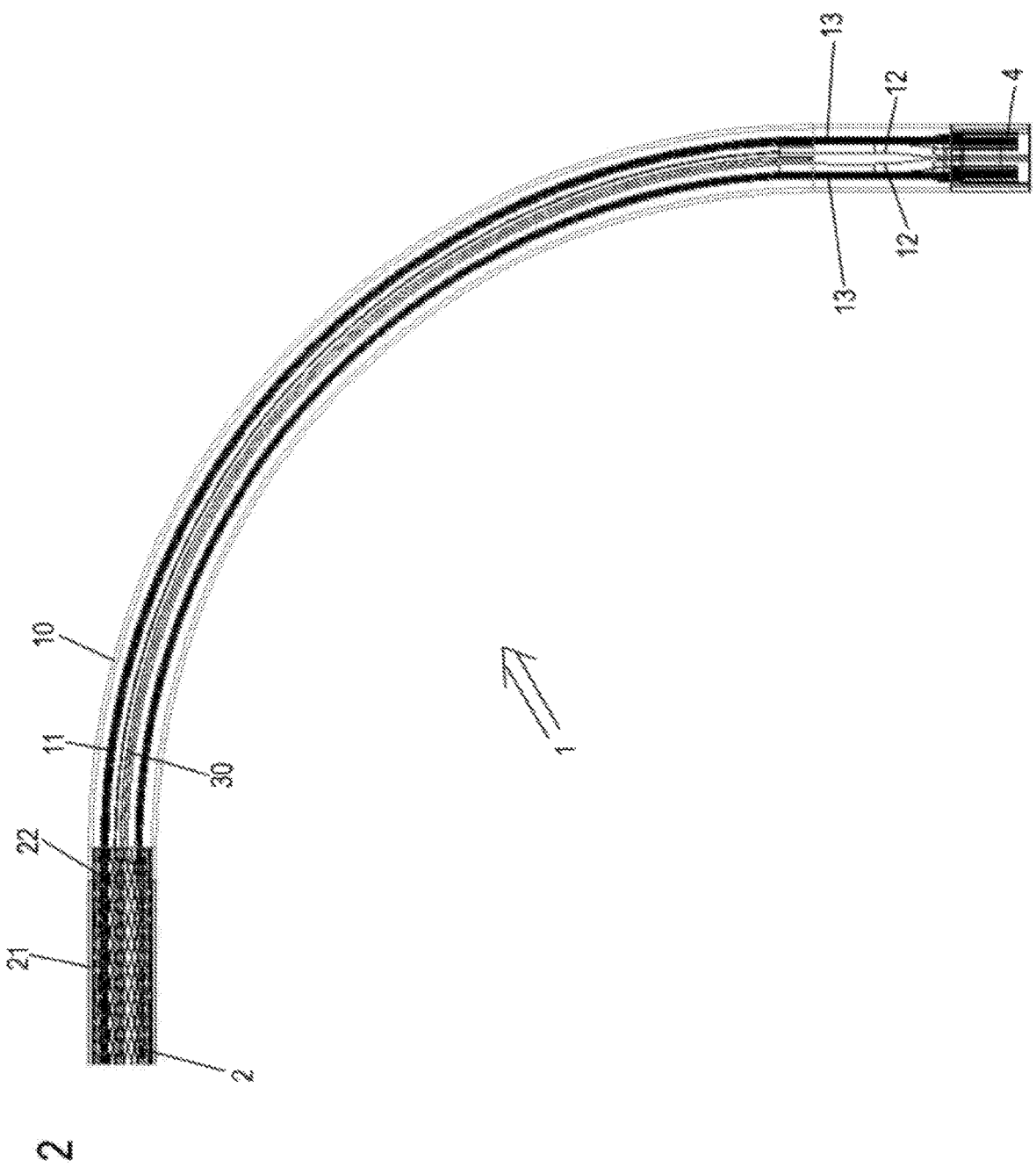
FIG. 2 shows a schematic side view of the interior of the bending portion in a first embodiment.

In the following, the present invention is described in detail with reference to the drawings on the basis of embodiments. The representations in the drawings are not necessarily true-to-scale, but are sometimes shown distorted for reasons of better clarity.

FIRST EMBODIMENT

Below, a first embodiment of the present invention is described with reference to the FIGS. 1 to 4(D).

An endoscope 1 according to the invention includes an insertion tube 2, a bending portion 3 and a distal end 4 on the distal side of a control member (not shown).

FIG. 1 illustrates a schematic side view of the distal region of the endoscope 1 according to the invention. On the distal side of the insertion tube 2, the bending portion 3 is disposed. On the distal side of the bending portion 3, the distal end 4 is disposed.

Insertion Tube 2

The insertion tube 2 is elastic and is intended to be inserted, distal end 4 first, into a patient for the purpose of examination. The insertion tube 2 is bendable to follow the bent openings of the body into which it is inserted. The insertion tube 2 is also sufficiently stiff and torsion-resistant so that it can be pushed past bends of the body openings. The insertion tube 2 includes a cover 21 on the outside and a wire mesh 22 preferably on the inside of the cover 21. The cover 21 protects the interior of the insertion tube 2. The wire mesh 22 imparts the required flexibility, stiffness and torsion resistance to the insertion tube 2.

Bending Portion 3

The bending portion 3 is located at the distal end of the insertion tube 2. The longitudinal direction of the bending portion 3 corresponds to the extension direction of the endoscope 1. The bending portion 3 is pivotable relative to the insertion tube 2. A pull rope 11 is used to pivot the bending portion 3. The pull rope 11 is actuated by being pulled from the proximal side. In the initial position in which the pull rope 11 is not pulled, the bending portion 3 is curved, as is exemplified in FIGS. 1 to 3.

In the bending portion 3, an elastic sleeve 10 extends from the distal end of the insertion tube 2 to the distal end 4. The elastic sleeve 10 is to be regarded as being a continuation of the cover 21 of the insertion tube 2 in the distal direction.

Separating Element 30

Figures 4A, 4B, 4C, 4D:
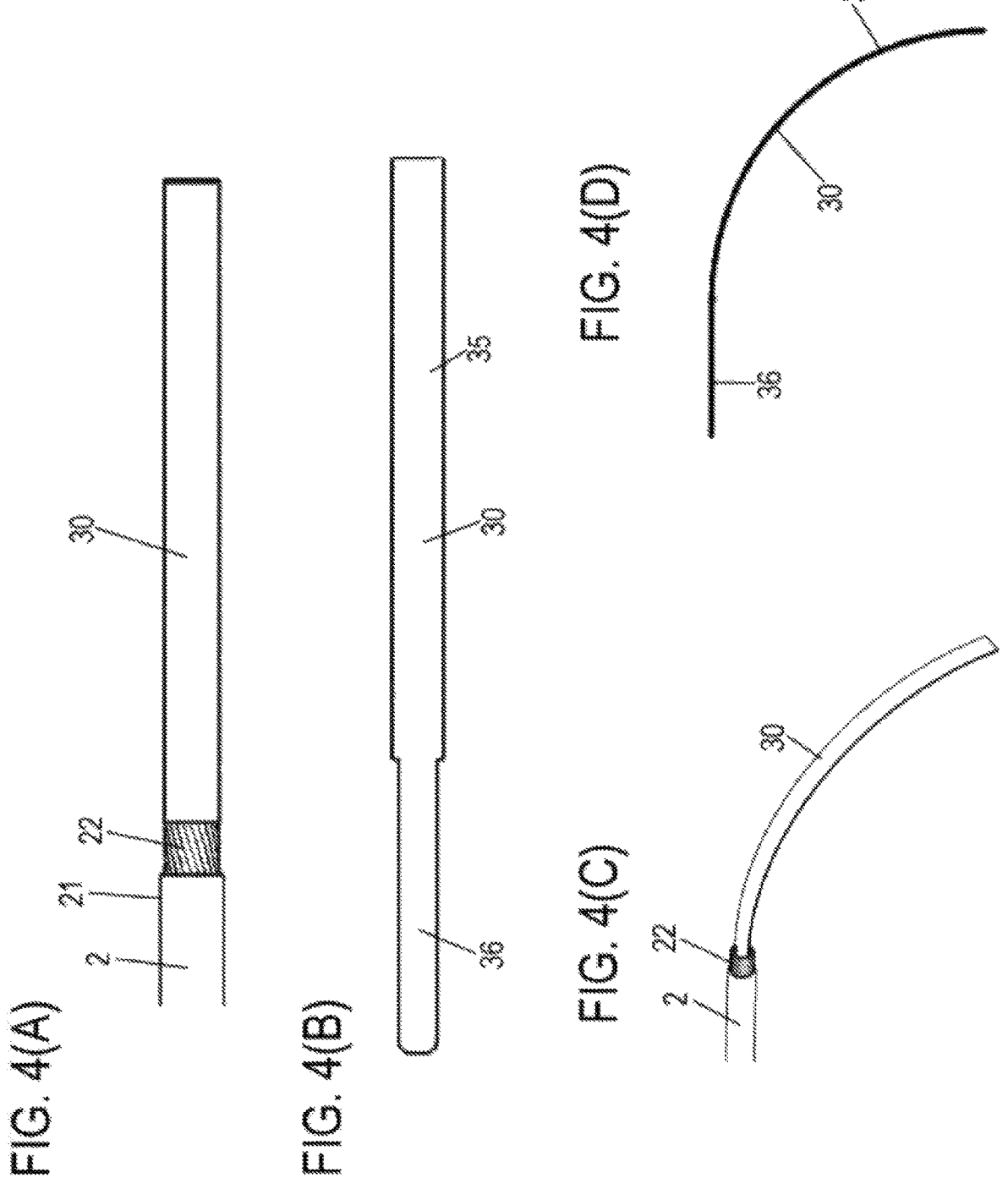
FIG. 4(A) shows how the flexible plate of the first embodiment is inserted in an insertion tube.
FIG. 4(B) shows a schematic top view onto a flexible plate of the first embodiment.
FIG. 4(C) shows a schematic perspective view of the flexible plate of the first embodiment inserted in the insertion tube.
FIG. 4(D) shows a schematic side view of the flexible plate of the first embodiment.

In the bending portion 3, a flat flexible plate 30 serving as a bendable plate is arranged as separating element 30. FIG. 4(B) illustrates an example of the flexible plate 30. In the top view, the flexible plate 30 takes the shape of an elongate rectangle. Moreover, the cross-section of the flexible plate 30 is formed as a rectangle. Thus, the cross-section of the flexible plate 30 has a short side and a long side. In the top view of FIG. 4(B), the flexible plate 30 is bendable toward the viewer and away from the viewer. At the unloaded initial stage, the flexible plate 30 is curved as can be seen from FIG. 4(C). The flexible plate 30 is curved so that the short side of the cross-section of the flexible plate 30 extends radially, i.e., along the extension of the radius of curvature. In an unloaded initial position, the flexible plate 30 is thus bent to the side, see FIG. 4(D). "Unloaded initial position" in this context means the state in which no force is applied to the flexible plate 30 and a pull rope is not pulled.

The flexible plate 30 has a narrower proximal portion 36 and a wider distal portion 35, when viewed in the longitudinal direction. The proximal portion 36 has a shorter width than the distal portion 35.

The proximal portion 36 is inserted from the distal side into the wire mesh 22 of the insertion tube 2. When inserting the flexible plate 30 into the wire mesh 22, the wider distal portion 35 can be used as a stop up to which the flexible plate 30 is inserted into the wire mesh 22. The length of the flexible plate 30 protruding from the wire mesh 22 is predefined in this way.

The proximal portion 36 may also be welded to or glued into or otherwise fastened to the wire mesh 22. Thus, the distal portion 35 of the flexible plate 30 protrudes in the distal direction from the wire mesh 22 of the insertion tube 2.

The sleeve 10 is drawn over the flexible plate 30. Accordingly, the outer edges of the distal portion 35 press into the elastic inner peripheral surface of the sleeve 10 so that the interior of the sleeve 10 is divided, in cross-section, into a first chamber 31 and a second chamber 32. In other words, the flexible plate 30 divides the interior of the sleeve 10. Each of the first chamber 31 and the second chamber 32 is delimited at the periphery by the inner peripheral surface of the sleeve 10 and by the flexible plate 30.

The first chamber 31 and the second chamber 32 extend in the longitudinal direction of the sleeve 10 from the distal end of the insertion tube 2 to the distal end 4. In the embodiment, the distal end of the flexible plate 30 is spaced apart from the proximal surface of the distal end 4, see FIG. 2. Alternatively, the distal end of the flexible plate 30 may abut on the proximal surface of the distal end 4 or may be anchored to the distal end 4.

The first chamber 31 and the second chamber 32 are thus separated from each other by the flexible plate 30. Preferably, the first chamber 31 and the second chamber 32 have the same cross-sectional size. Hence, the flexible plate 30 divides the interior of the sleeve 10 into two equal halves. As an alternative, the flexible plate 30 can divide the interior of the sleeve 10 into two halves of different size, in that case the first chamber 31 and the second chamber 32 have a different cross-sectional size.

Figures 3A, 3B:
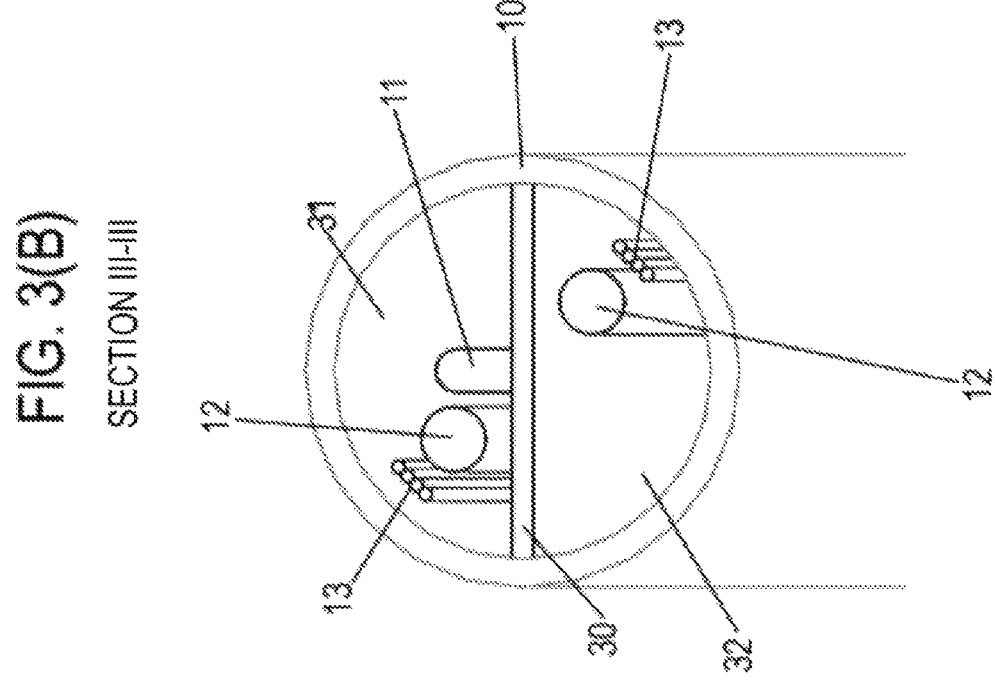
FIG. 3(A) shows another schematic side view of the interior of the bending portion of the first embodiment.
FIG. 3(B) shows a schematic sectional view across the bending portion of the first embodiment along a section III-III of FIG. 3(A).

As illustrated in FIG. 3(B), in the first chamber 31, a pull rope 11, a camera cable 12 and a light conductor 13 are arranged so that they extend in the longitudinal direction of the bending portion 3 in parallel to the bent axis of the bending portion 3. In the second chamber 32, a camera cable 12 and a light conductor 13 are arranged so that they extend in the longitudinal direction of the bending portion 3 in parallel to the bent axis of the bending portion 3. In the second chamber 32 there is no pull rope arranged.

The flexible plate 30 is bendable and may be manufactured from spring steel, stainless steel or bendable plastic material. Despite the bendability, the flexible plate 30 is neither compressible nor expandable. The flexible plate 30 thus has a function similar to that of a spinal column.

Pulling of the pull rope 11 in the proximal direction causes the bending portion 3 bent in the unloaded state to be bent in the direction in which the bending portion 3 becomes straight. In other words, pulling of the pull rope 11 in the proximal direction causes the bending portion 3 to stretch.

Distal End 4

The distal end 4 may act as an endoscope head. In the distal end 4, the pull rope 11 is anchored. On the distal side of the distal end 4, an optical system (not shown) and a camera (not shown) are disposed. The optical system is connected to the light conductor 13 and ensures illumination of a scenery to be viewed. The camera is connected to the camera cable 12 and takes pictures of the illuminated scenery.

The sleeve 10 may abut on the distal end 4 or, alternatively, cover the outer peripheral side of the distal end 4.

The endoscope 1 according to the invention may be very small. The outer diameter of the insertion tube 2, of the sleeve 10 of the bending portion 3 and of the distal end 4 may be 3 mm or less. In an even smaller design, the outer diameter of the insertion tube 2, of the sleeve 10 of the bending portion 3 and of the distal end 4 may even be 2 or 1 mm or less.

Function of the Invention

By pulling the pull rope 11 in the proximal direction, the distance between the distal end of the insertion tube 2 and the distal end 4 is reduced. When the single pull rope 11 disposed in the first chamber 31 is pulled, the flexible plate 30 is bent to the side where the first chamber 31 is located. Therefore, the bending portion 3 pivots to the side where the bending portion 3 adopts a straight, i.e., expanded, shape (to the left in FIG. 3(A)). By pulling the pull rope 11, the bending portion 3 finally can adopt a completely straight shape. When the bending portion 3 has adopted a completely straight shape and the pull rope 11 is continued to be pulled in the proximal direction, the bending portion 3 is curved in the direction (to the left in FIG. 3(A)) opposed to the direction of its initial curvature.

Advantages of the Invention

The bending portion 3 shows a very simple design, makes use of few components and, therefore, can be manufactured at very low cost.

The bending portion 3 requires no eyelets or other pull rope guide elements as a rope guideway. This is particularly advantageous for thin insertion tubes, because no cavity must be made available for the eyelets. The flexible plate 30 divides the interior of the bending portion 3 into the two chambers 31 and 32. The chamber 31 serves as rope guideway for the pull rope 11. Consequently, the pull rope 11 is safely guided.

The bending portion 3 can attain any desired curved position by pulling the one pull rope 11. Nevertheless, for this purpose only one single pull rope 11 is required. Therefore, the space that would be necessary for further pull ropes is saved. Hence, the bending portion 3 and, consequently, the entire endoscope can be built with an even smaller diameter.

Thus, the bending portion 3 according to the invention can be used for an endoscope comprising a very small insertion tube.

SECOND EMBODIMENT

Figure 7:
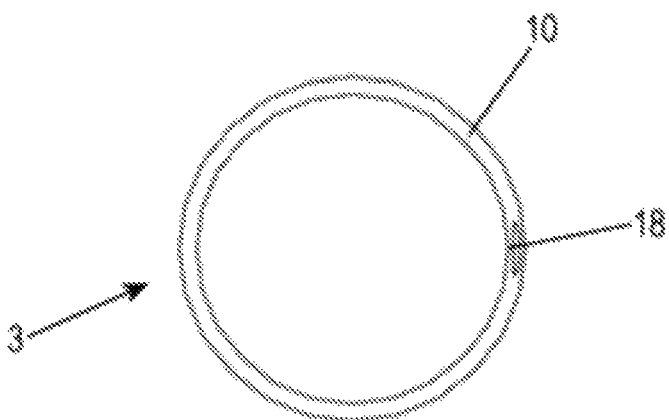
FIG. 7 shows a schematic sectional view across the sleeve of the second embodiment.

In the following, a second embodiment of the present invention is described with reference to the FIGS. 5 to 7.

In the second embodiment, a spring element 18 for anti-torsion protection is arranged in the sleeve 10 of the first embodiment.

Otherwise, the structure of the second embodiment resembles that of the first embodiment.

Figures 5, 6:
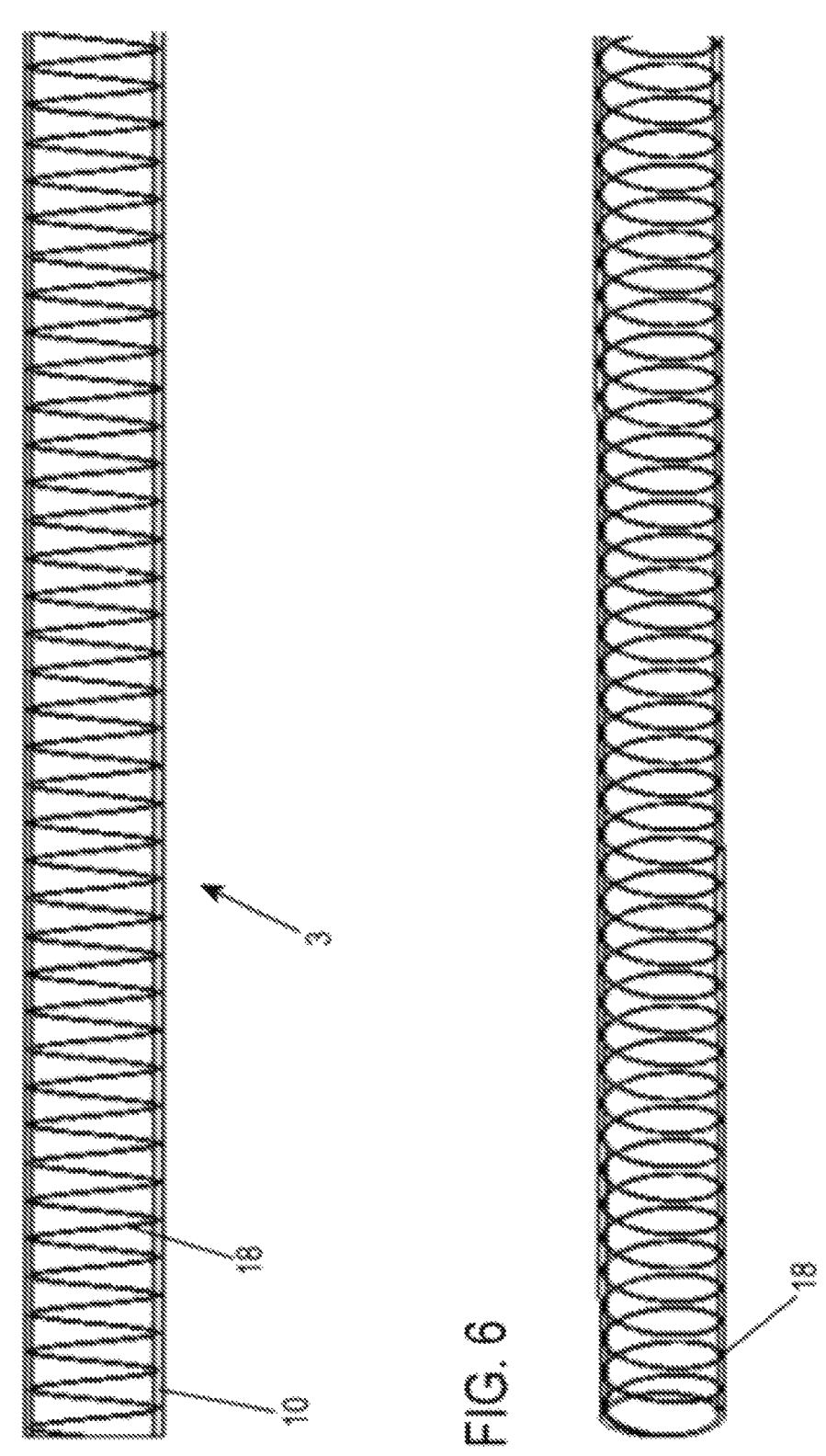
FIG. 5 shows a schematic side view of a sleeve of the bending portion in a second embodiment.
FIG. 6 shows a schematic perspective view of the spring element of the second embodiment.

FIG. 5 illustrates a schematic side view of the sleeve 10 of a bending portion 3 of the second embodiment. For reasons of clarity, the pull rope 11 and the bendable plate 30 are not shown, nor are the camera cable 12 and the light conductor 13 represented.

In order to impart advantageous bendability to the sleeve 10, a spring element 18 shown in FIG. 6 is embedded in the interior of the sleeve 10. In FIG. 7, the position of the spring element 18 is indicated in the cross-section of the sleeve 10 of the second embodiment.

The sleeve 10 of the second embodiment can be manufactured so that plastic material is cast or extruded onto the spring element 18 such that the spring element 18 is sandwiched between the inner peripheral surface and the outer peripheral surface of the sleeve 10 made from the plastic material.

The sleeve 10 of the second embodiment may thus be configured to be bendable but also stiff and torsion-resistant.

Moreover, the same advantages are resulting as in the first embodiment.

THIRD EMBODIMENT

In the following, a third embodiment of the present invention is described with reference to FIG. 8.

Figure 8:
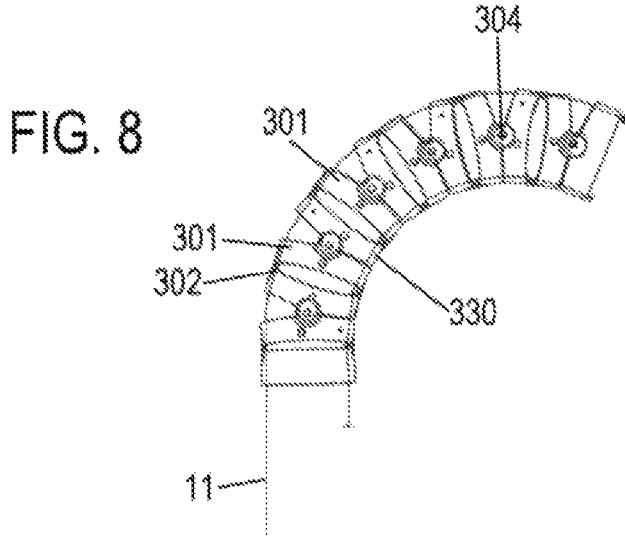
FIG. 8 shows a schematic side view of the interior of the bending portion in a third embodiment.

FIG. 8 illustrates a schematic side view of the interior of the bending portion in a third embodiment.

The bending portion of the third embodiment can make use of the cover 21 of the first or second embodiment. This is also applicable to the following embodiments.

The bending portion of the third embodiment moreover makes use of a known articulated structure and includes articulated rings 301. Plural articulated rings 301 are disposed along the longitudinal direction of the bending portion. Adjacent articulated rings 301 are coupled to each other by an articulation 304 so that they are pivotable relative to each other about the axis of the articulation 304. Therefore, each pair of adjacent articulated rings 301 has two articulations 304 located spaced apart from each other by 180 degrees, i.e., at diagonal positions on the articulated rings 301. The first articulated ring 301 at the proximal end of the bending portion includes the two articulations 304 on the distal side only. The last articulated ring 301 at the distal end of the bending portion includes the two articulations 304 on the proximal side only. The radial outside of the articulated structure made of the articulated rings 301 is covered by the cover (not shown).

Each articulated ring 301 has a right eyelet 302 and a left eyelet 302 on its periphery. More precisely, the respective eyelet 302 is formed on the inner peripheral surface of the respective articulated ring 301. The respective eyelet 302 forms an opening extending in the longitudinal direction of the bending portion. In said opening, a pull rope described below or a pre-bent spring rod described below can be received. The eyelets 302 are indicated merely schematically in FIG. 8.

The right eyelet 302 is arranged on the side opposite to the left eyelet 302. In other words, the position of the right eyelet 302 on the articulated ring 301 is spaced apart from the left eyelet 302 by 180 degrees, i.e., they are arranged at diagonal positions on the articulated ring 301. When viewed in the longitudinal direction of the bending portion, all of the left eyelets 302 are arranged in a row. Equally, when viewed in the longitudinal direction of the bending portion, all of the right eyelets 302 are arranged in a row.

In FIG. 8, the left eyelets 302 are arranged on the left side of the articulated rings 301, and the right eyelets 302 are arranged on the right side of the articulated rings 301.

In the present third embodiment, a pull rope 11 is guided in the left eyelets 302 of the articulated rings 301. In the present third embodiment, a pre-bent spring rod 330 is guided in the right eyelets 302 of the articulated rings 301. The distal end of the pull rope 11 is fixed to the last articulated ring 301 at the distal end of the bending portion. The distal end of the pre-bent spring rod 330 is fixed to the last articulated ring 301 at the distal end of the bending portion. The spring rod 330 constitutes an additional element that is used in addition to the pull rope in the bending portion.

The pre-bent spring rod 330 is a spring wire.

The pre-bent spring rod 330 is pre-bent toward a bending side, i.e., to the right in FIG. 8. In the embodiment, the pre-bent spring rod 330 is pre-bent by about 90 degrees, for example. The pre-bending angle can be selected as desired, however.

The pre-bending of the pre-bent spring rod 330 imparts a presetting bent to the side, i.e., to the right in FIG. 8, in the non-actuated state in the present third embodiment. In this non-actuated state, the right sides of the articulated rings 301 may abut on each other or may have a minimum distance, while the left sides of the articulated rings 301 are maximally spaced from each other.

The pre-bent spring rod 330 has such length that, in the afore-described non-actuated state, it protrudes at the first articulated ring 301 at the proximal end of the bending portion in the proximal direction, as shown in FIG. 8. The portion of the pre-bent spring rod 330 protruding in the non-actuated state to the proximal side on the first articulated ring 301 has a straight extension, see FIG. 8. The pre-bent spring rod 330 is arranged in the right eyelets 302 of the articulated rings 301 such that the pre-bent spring rod 330 is slidable relative to the right eyelets 302 of the articulated rings 301.

The pull rope 11 is guided in the left eyelets 302 or the articulated rings 301. If, starting from the non-actuated state in FIG. 8, the pull rope 11 is pulled in the proximal direction, the left sides of the articulated rings 301 are rotated about the articulations 304 and pulled toward each other. Since the distal end of the pre-bent spring rod 330 is fixed to the last articulated ring 301 at the distal end of the bending portion and the pre-bent spring rod 330 is slidable relative to the right eyelets 302 of the articulated rings 301, the articulated rings 301 can be pivoted about the articulations 304. In so doing, the distance of the articulated rings 301 increases on the right side thereof. The pre-bent spring rod 330 guided in the right eyelets 302 does not prevent the distance of the articulated rings 301 from increasing on the right side thereof, as it is slidably supported in the right eyelets 302.

Thus, by pulling the pull rope 11 the bending portion can be brought into a stretched position in which the articulated rings 301 are aligned in parallel to each other.

When, starting from the stretched position, the pull rope 11 is continued to be pulled in the proximal direction, the left sides of the articulated rings 301 are continue to be rotated (pivoted) about the articulations 304 and pulled toward each other until they abut on each other. In this situation, the articulated rings 301 are maximally spaced apart from each other on the right side thereof.

The straight portion of the pre-bent spring rod 330 in the non-actuated state protruding to the proximal side on the first articulated ring 301 has such length that, considering FIG. 8, the bending portion can be bent at least 90 degrees to the left by pulling the pull rope 11. The straight portion of the pre-bent spring rod 330 in the non-actuated state protruding to the proximal side on the first articulated ring 301 may also be designed to be longer. Considering FIG. 8, the bending portion then can be bent more than 90 degrees to the left by pulling the pull rope 11. The straight portion of the pre-bent spring rod 330 in the non-actuated state protruding to the proximal side on the first articulated ring 301 can also be designed to be shorter. Considering FIG. 8, the bending portion then can be bent less than 90 degrees to the left by pulling the pull rope 11. The pre-bent spring rod 330 can be provided with a stop at the proximal end so that the proximal end of the pre-bent spring rod 330 cannot slip through the right eyelet 302 of the first articulated ring 301.

FOURTH EMBODIMENT

In the following, a fourth embodiment of the present invention is described with reference to FIG. 9.

Figure 9:
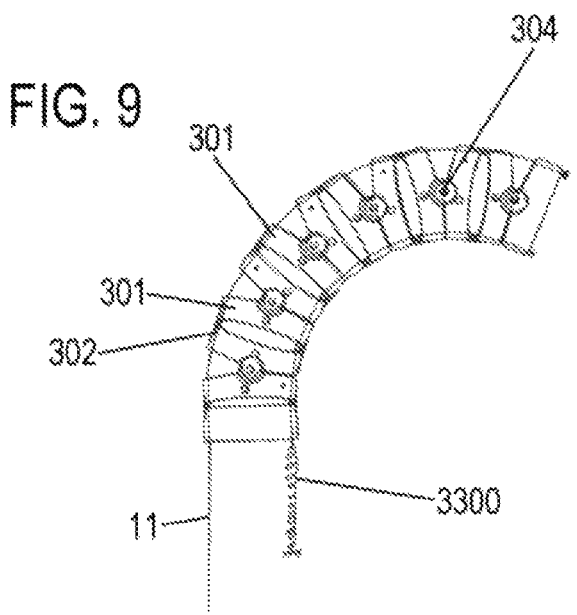
FIG. 9 shows a schematic side view of the interior of the bending portion in a fourth embodiment.

FIG. 9 illustrates a schematic side view of the interior of the bending portion in a fourth embodiment.

The bending portion of the fourth embodiment equally makes use of the known articulated structure explained in the third embodiment and includes articulated rings 301. Plural articulated rings 301 are arranged along the longitudinal direction of the bending portion. Adjacent articulated rings 301 are coupled to each other by an articulation 304 so that they are pivotable toward each other about the axis of the articulation 304. Therefore, each pair of adjacent articulated rings 301 has two articulations 304 which are located spaced apart from each other by 180 degrees, i.e., at diagonal positions on the articulated rings 301. The first articulated ring 301 at the proximal end of the bending portion has the two articulations 304 on the distal side only. The last articulated ring 301 at the distal end of the bending portion has the two articulations 304 on the proximal side only.

Each articulated ring 301 has a right eyelet 302 and a left eyelet 302 on its periphery. The right eyelet 302 is arranged on the side opposite to the left eyelet 302. In other words, the position of the right eyelet 302 on the articulated ring 301 is spaced apart from the left eyelet 302 by 180 degrees, i.e., they are arranged at diagonal positions on the articulated ring 301. When viewed in the longitudinal direction of the bending portion, all of the left eyelets 302 are arranged in a row. Equally, when viewed in the longitudinal direction of the bending portion, all of the right eyelets 302 are arranged in a row.

In FIG. 9, the left eyelets 302 are arranged on the left side of the articulated rings 301, and the right eyelets 302 are arranged on the right side of the articulated rings 301.

In the fourth embodiment, a pull rope 11 is guided in the left eyelets 302 of the articulated rings 301. In the fourth embodiment, a distal guided pull rope (not shown because hidden in FIG. 8) is guided in the right eyelets 302 of the articulated rings 301. The distal end of the pull rope 11 is fixed to the last articulated ring 301 at the distal end of the bending portion. The distal end of the distal guided pull rope is fixed to the last articulated ring 301 at the distal end of the bending portion. On the proximal side, a proximal spiral spring element 3300 is arranged on (connected) to the distal guided pull rope. Said spiral spring element 330 forms an additional element. The pulling of the spiral spring element 3300 predefines the bending direction of the bending portion.

Basically, the fourth embodiment differs from the third embodiment by the fact that, instead of the pre-bent spring rod 330, a combination of a distal guided pull rope and a proximal spiral spring element 3300 is provided. The remaining aspects are the same. The explanations made concerning the third embodiment are also applicable to the fourth embodiment. The combination of the distal guided pull rope and the proximal spiral spring element 3300 virtually constitutes a combined pull rope body which is pulled as a whole. The proximal spiral spring element 330 is under tension already in the non-actuated initial state. Thereby, the combination of the distal guided pull rope and the proximal spiral spring element 3300 is in a biased state that bends the bending portion already in the non-actuated initial state to the radial side, see FIG. 9, on which the combination of the distal guided pull rope and the proximal spiral spring element 3300 is arranged in the bending portion.

The distal guided pull rope can have a length, for example, that runs through the biased bending portion, wherein the connecting point to the proximal spiral spring element 3300 may be provided at the proximal end of the bending portion, in front of or behind the proximal end of the bending portion. In the afore-described non-actuated state, the proximal spiral spring element 3300 protrudes on the first articulated ring 301 at the proximal end of the bending portion in the proximal direction or is located proximally from the bending portion, as shown in FIG. 9.

The length of the combination of the distal guided pull rope and the proximal spiral spring element 3300 can be selected to be similar to the length of the pre-bent spring rod 330 of the third embodiment.

The proximal spiral spring element 3300 is expandable. The proximal spiral spring element 3300 acts as a tension spring.

The proximal spiral spring element 3300 is biased so that the bending portion is pre-bent to one bending side, i.e., to the right in FIG. 9. In the embodiment, in this way the bending portion is pre-bent by about 90 degrees, for example. The pre-bending angle may be selected as desired, however.

Due to the bias of the proximal spiral spring element 3300, the bending portion in the present fourth embodiment thus in the non-actuated state has a presetting bent to the side, i.e., to the right in FIG. 9. In this non-actuated state, the right sides of the articulated rings 301 abut on each other, whereas the left sides of the articulated rings 301 are maximally spaced apart from each other.

In the left eyelets 302 of the articulated rings 301 the pull rope 11 is guided. When, starting from the non-actuated state in FIG. 9, the pull rope 11 is pulled in the proximal direction, the left sides of the articulated rings 301 are rotated about the articulations 304 and are pulled toward each other. In so doing, on the right sides of the articulated rings 301 held together by the bias of the proximal spiral spring element 3300, the combination of the distal guided pull rope and the proximal spiral spring element 3300 is stretched (i.e., only the proximal spiral spring element 3300 is stretched) so that the right sides of the articulated rings 301 move away from each other, as the articulated rings 301 are rotated about the articulations 304.

Thus, by pulling the pull rope 11 the bending portion can be brought into a stretched position in which the articulated rings 301 are aligned in parallel to each other.

When, starting from the stretched position, the pull rope 11 is continued to be pulled in the proximal direction, the left sides of the articulated rings 301 are continued to be rotated about the articulations 304 and pulled toward each other until they abut on each other. In this situation, the right sides of the articulated rings 301 are maximally spaced from each other, and the proximal spiral spring element 3300 is maximally stretched. In this situation, the bending portion does not face as shown in FIG. 9, but to the left.

FIFTH EMBODIMENT

In the following, a fifth embodiment of the present invention is described with reference to FIG. 10.

Figure 10:
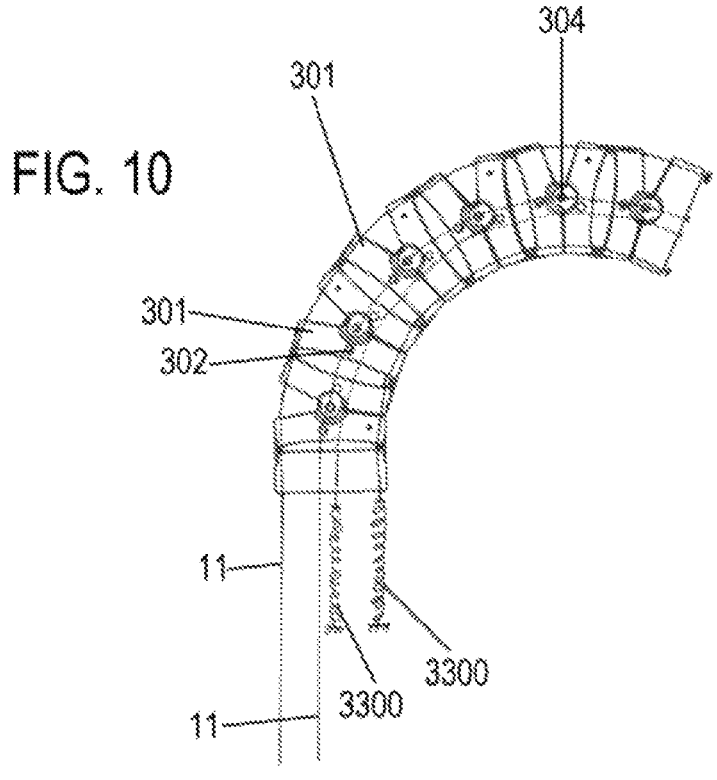
FIG. 10 shows a schematic side view of the interior of the bending portion in a fifth embodiment.

FIG. 10 illustrates a schematic side view of the interior of the bending portion in a fifth embodiment.

The fifth embodiment constitutes a further development of the fourth embodiment. In the fourth embodiment, a pull rope 11 is guided in the left eyelets 302 of the articulated rings 301, and a combination of the distal guided pull rope and the proximal spiral spring element 3300 is guided in the right eyelets 302 of the articulated rings 301.

In the present fifth embodiment, in addition to the structure of the fourth embodiment, further eyelets are arranged offset by 90 degrees on each articulated ring 301. On each articulated ring 301, four eyelets are arranged evenly distributed along the periphery and offset by 90 degrees. When viewed in the longitudinal direction of the bending portion, all of the left eyelets 302 are arranged in a row. Further, when viewed in the longitudinal direction of the bending portion, all of the right eyelets 302 are arranged in a row. Moreover, when viewed in the longitudinal direction of the bending portion, all of the front eyelets 302 are arranged in a row. Finally, when viewed in the longitudinal direction of the bending portion, all of the rear eyelets 302 are arranged in a row.

In the left eyelets 302 of the articulated rings 301, a first pull rope 11 is guided. In the right eyelets 302 of the articulated rings 301, a first biased combination of the distal guided pull rope and the proximal spiral spring element 3300 is guided. In the front eyelets 302 of the articulated rings 301, a second pull rope 11 is guided. In the rear eyelets 302 of the articulated rings 301, a second biased combination of the distal guided pull rope and the proximal spiral spring element 3300 is guided. More precisely, in each of the respective combinations of the distal guided pull rope and the proximal spiral spring element 3300, the distal guided pull rope is guided in the eyelets and the proximal spiral spring element 3300 ensures the bias.

Adjacent articulated rings 301 pivot toward each other about the articulations 304. In the present invention, the articulation 304 is meant to be a bearing that permits an articulated ring 301 to be pivoted to the adjacent articulated ring 301. The articulation 304 includes a pivot axis about which an articulated ring 301 pivots to the adjacent articulated ring 301.

Adjacent articulated rings 301 are coupled to each other by an articulation 304 such that they are pivotable toward each other about the axis of the articulation 304. Except for the first articulated ring 301 at the proximal end of the bending portion and the last articulated ring 301 at the distal end of the bending portion, each articulated ring 301 includes, on the proximal side, two articulations 304 which are spaced apart from each other by 180 degrees, i.e., at diagonal positions on the articulated rings 301. On the distal side, each articulated ring 301 includes, on the proximal side, two articulations 304 which are equally spaced apart from each other by 180 degrees, i.e., at diagonal positions on the articulated rings 301. The articulations 304 on the distal side are arranged offset by 90 degrees at the periphery of the articulated ring 301 relative to the articulations 304 on the proximal side.

When viewed in the proximal and distal directions, the position of the two articulations 304 is therefore provided to be rotated about 90 degrees on the articulated ring 301 next in the proximal and distal directions. The articulated rings 301 thus can pivot relative to each other not only to the left and the right but also to the front and the rear.

The first articulated ring 301 at the proximal end of the bending portion includes the two articulations 304 on the distal side only. The last articulated ring 301 at the distal end includes the two articulations 304 on the proximal side only.

In the fourth embodiment, considering FIG. 8, the bending portion can pivot to the right and the left and, consequently, in two directions. In the present fifth embodiment, considering FIG. 9, the bending portion can pivot to the right and the left and to the front (toward the viewer) and the rear (away from the viewer) and, consequently, in four directions.

In the rear eyelets 302 and in the right eyelets 302, the first and second combinations of the distal guided pull rope and the proximal spiral spring element 3300 are arranged to be biased. Hence, in the non-actuated state in FIG. 9, the respective region of adjacent articulated rings 301 located between the rear eyelets 302 and the right eyelets 302 is abutting or has a minimum distance.

When, starting from the non-actuated state in FIG. 9, the first and second pull ropes 11 are evenly pulled in the proximal direction, the left and front sides of the articulated rings 301 are rotated (pivoted) about the articulations 304 and are pulled toward each other. In so doing, on the right and rear side of the articulated rings 301 held together by the first and second biased combinations of the distal guided pull rope and the proximal spiral spring element 3300, the first and second biased proximal spiral spring element 3300 is pulled (stretched and thus expanded) such that the right and rear sides of the articulated rings 301 move apart from each other, because the articulated rings 301 are rotated (pivoted) about the articulations 304.

If only the first pull rope 11 is pulled in the proximal direction, the distal end of the bending portion moves to the left.

If only the second pull rope 11 is pulled in the proximal direction, the distal end of the bending portion moves to the front (toward the viewer).

Combined pulling and relieving movements of the first pull rope 11 and the second pull rope 11 allow the distal end of the bending portion to pivot in the desired direction in the three-dimensional space.

The bending portion at the distal end 4 can be bent equally to the right and the left and to the front (toward the viewer) and the rear (away from the viewer), consequently in four directions and all intermediate directions therebetween.

SIXTH EMBODIMENT

In the following, with reference to FIG. 11, a sixth embodiment of the present invention is described.

Figure 11:
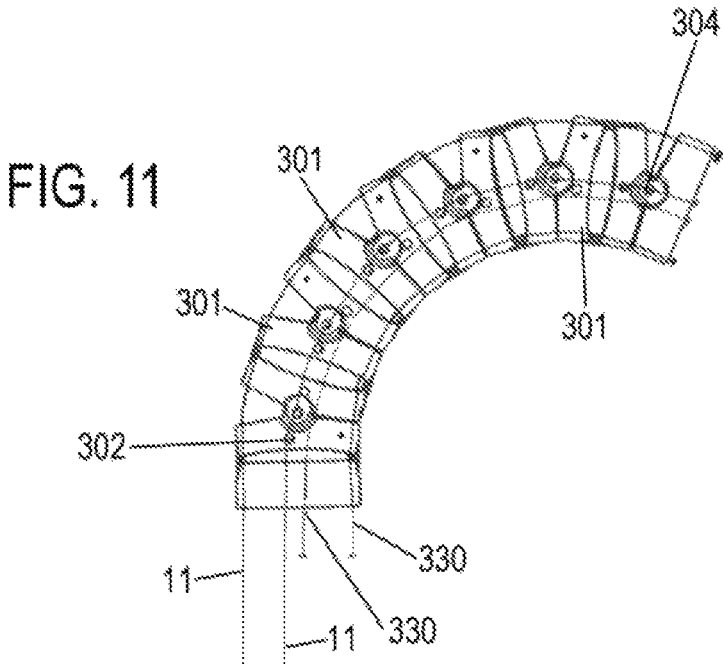
FIG. 11 shows a schematic side view of the interior of the bending portion in a sixth embodiment.

FIG. 11 illustrates a schematic side view of the interior of the bending portion in a sixth embodiment.

The sixth embodiment is a further development of the third embodiment. In the third embodiment, a pull rope 11 is guided in the left eyelets 302 of the articulated rings 301, and in the right eyelets 302 of the articulated rings 301 the pre-bent spring rod 330 is guided which is configured as an elastic wire.

In the present sixth embodiment, similarly to the fifth embodiment, in addition to the structure of the third embodiment further eyelets are arranged on each articulated ring 301 offset by 90 degrees. On each articulated ring 301, four eyelets being evenly distributed along the periphery are arranged offset by 90 degrees. When viewed in the longitudinal direction of the bending portion, all of the left eyelets 302 are arranged in a row. Further, when viewed in the longitudinal direction of the bending portion, all of the right eyelets 302 are arranged in a row. Moreover, when viewed in the longitudinal direction of the bending portion, all of the front eyelets 302 are arranged in a row. Finally, when viewed in the longitudinal direction of the bending portion, all of the rear eyelets 302 are arranged in a row.

In the left eyelets 302 of the articulated rings 301 a first pull rope 11 is guided. In the right eyelets 302 of the articulated rings 301 a first pre-bent spring rod 330 is guided. In the front eyelets 302 of the articulated rings 301 a second pull rope 11 is guided. In the rear eyelets 302 of the articulated rings 301 a second pre-bent spring rod 330 is guided. The first pre-bent spring rod 330 and the second pre-bent spring rod 330 are configured as a pre-bent spring wire.

Adjacent articulated rings 301 pivot relative to each other about the articulations 304 as in the fifth embodiment.

The pre-bent spring rods 330 are pre-bent to the right in a way similar to the third embodiment. For example, the pre-bent spring rods 330 are pre-bent by about 90 degrees. The pre-bending angle may be selected as desired, however.

Due to the pre-bend of the pre-bent spring rods 330, the bending portion has a presetting bent to the side, i.e., to the right in FIG. 11, in the non-actuated state. In said non-actuated state, the sides of the articulated rings 301 which are opposed to the pull ropes 11 abut on each other as in the fifth embodiment. In said non-actuated state, the sides of the articulated rings 301 on which the pre-bent spring rods 330 are arranged to be guided in their eyelets 302 are maximally spaced apart from each other.

The two pre-bent spring rods 330 have, as in the firth embodiment, such a length that, in the afore-described non-actuated state, they protrude on the first articulated ring 301 at the proximal end of the bending portion in the proximal direction, as illustrated in FIG. 11. The portion of the pre-bent spring rods 330 protruding to the proximal side on the first articulated ring 301 in the non-actuated state has a straight extension, see. FIG. 11. The pre-bent spring rods 330 are arranged in the right eyelets 302 of the articulated rings 301 and in the rear eyelets 302 of the articulated rings 301 so that the pre-bent spring rods 330 are slidable relative to the right eyelets 302 of the articulated rings 301 and to the rear eyelets 302 of the articulated rings 301.

Hence, the structure and the function of the sixth embodiment corresponds to a combination of the third and fifth embodiments.

In the sixth embodiment, considering FIG. 11, the bending portion can pivot to the right and the left and to the front (toward the viewer) and the rear (away from the viewer) and, consequently, in four directions and all intermediate directions therebetween.

Further Alternatives

In the first embodiment, a pull rope 11 is arranged in the first chamber 31 arranged on the radially outer side with respect to the bend of the plate 30. There is no pull rope in the second chamber 32 arranged on the radially inner side with respect to the bend of the plate 30. The principle of the invention can also be applied to a structure in which two or more pull ropes 11 are arranged in the first chamber 31 arranged on the radially outer side with respect to the bend of the plate 30. Even in this alternative, there is no pull rope in the second chamber 32 arranged on the radially inner side with respect to the bend of the plate 30.

In the second embodiment, a spring element 18 is interposed between the inner peripheral surface and the outer peripheral surface of the sleeve 10. In one alternative, a spring element may be disposed on the inner peripheral surface of the sleeve 10 to impart a desired elasticity and bending stiffness to the sleeve 10.

In the first embodiment, the elastic sleeve 10 of the bending portion 3 forms a continuation of the cover 21 of the insertion tube 2 in the distal direction. In one alternative, the elastic sleeve 10 and the cover 21 can be a one-piece cover extending from the control member of the endoscope to the distal end 4.

In the first embodiment, the flexible plate 30 is in the form of an elongate rectangle. The flexible plate 30 may also take other shapes. The cross-section of the bendable plate 30 may take a rectangular, oval, elliptic or race-track shape etc. The race-track shape (or stadium shape) has linear segments inserted between semicircular-type end pieces. Thus, one side of the separating element is longer than the other side. The separating element bends about the thinner side. In this way, when pulling the pull rope the bending direction is predetermined.

In the embodiments, the separating element is in the form of a flexible or bendable plate. The invention is not limited thereto. The separating element may also be produced as a partition already when the sleeve 10 is manufactured by extrusion, for example. In this case, the separating element is integrally connected to the sleeve 10. For achieving sufficient push stability, a wire mesh may be integrated in the separating element.

In the third to sixth embodiments, eyelets are used as pull rope guide elements. The invention is not limited thereto. For guiding the pull rope also differently structured pull rope guide elements can be used. For example, pull rope guide elements having an open, semi-open or closed guide body can be used. Eyelets are examples of a closed guide body. The guide body for guiding the pull rope need not be completely closed. In the open or semi-open design, the guide body has an incomplete enclosure that does not completely enclose the guided pull rope.

In an alternative of the fourth and sixth embodiments, the combination of a distal guided pull rope and a proximal spiral spring element 3300 is replaced by a spiral spring element 3300. In this alternative, a biased spiral spring 3300 is guided in the right eyelets 302 of the articulated rings 301. The distal end of the biased spiral spring 3300 is fixed to the last articulated ring 301 at the distal end of the bending portion. The biased spiral spring 3300 has such length that, in the afore-described non-actuated state, it may protrude in the proximal direction on the first articulated ring 301 at the proximal end of the bending portion, as illustrated in FIG. 9.

In the embodiments, both the optical system including the light conductor 13 and the camera including the camera cable 12 are merely examples of use for the endoscope according to the invention and can be modified or even omitted.

As an alternative, when the invention is applied to a larger endoscope, a working duct, a rinsing duct and/or an ultrasonic sensor etc. can be installed.

The invention can be advantageously applied to a flexible endoscope. The principle of the invention can be applied to any type of endoscope comprising a bending portion.

LIST OF REFERENCE NUMERALS

1 endoscope
2 insertion tube
3 bending portion
4 distal end
10 sleeve
11 pull rope
12 camera cable
13 light conductor
18 spring element
21 cover
22 wire mesh
30 separating element
31 first chamber
32 second chamber
35 distal portion of the bendable plate
36 proximal portion of the bendable plate
301 articulated ring
302 eyelet
304 articulation
330 pre-bent spring rod
3300 spiral spring

The invention claimed is:

1. An endoscope comprising:

a flexible insertion tube; and a bending portion comprising a sleeve and controllable from a proximal side, the bending portion being distally connected to the insertion tube, wherein in the bending portion at least one pull rope longitudinally extends to provide for a pivoting movement of the bending portion, the at least one pull rope being anchored to a distal end of the bending portion, wherein a biased bendable divider dividing a cross-section of the sleeve into separate first and second chambers having the same cross sectional size is arranged in a longitudinal direction of the bending portion in parallel to the at least one pull rope, the divider having a predefined bend toward one side of the bending portion such that the bending portion is pre-bent to the one side, wherein the at least one pull rope is arranged in only the first chamber, wherein in a pre-bent state of the bending portion, the first chamber is located outside of a radius of the divider, and wherein the second chamber includes at least one of a camera cable and a light conductor and is inside of the radius of the divider.

2. The endoscope according to claim 1, wherein the divider is anchored on its proximal side to a distal end region of the insertion tube.

3. The endoscope according to claim 2, wherein the insertion tube has an outer cover and, beneath the outer cover, an elastic wire mesh, the proximal side of the divider being anchored to a distal end region of the wire mesh, and the proximal side of the divider is inserted into, welded to or glued into the distal end region of the wire mesh.

4. The endoscope according to claim 1, wherein the sleeve of the bending portion has an outer diameter of 3 mm or less.

5. The endoscope according to claim 1, wherein the sleeve of the bending portion has an outer diameter of 1 mm or less.

6. The endoscope according to claim 1, wherein the divider is made from spring steel, stainless steel or a bendable plastic material.

7. The endoscope according to claim 1, wherein the sleeve of the bending portion includes a spring element embedded therein.

8. The endoscope according to claim 1, wherein a cross-section of the divider is wider in a first direction and is narrower in a second direction being perpendicular to the first direction.

\* \* \* \* \*